United States Patent
Papp et al.

(10) Patent No.: US 10,549,115 B2
(45) Date of Patent: Feb. 4, 2020

(54) VOLUMETRIC MODULATED ARC THERAPY (VMAT) WITH NON-COPLANAR TRAJECTORIES

(71) Applicants: KONINKLIJKE PHILIPS N.V., Eindhoven (NL); The General Hospital Corporation, Boston, MA (US)

(72) Inventors: David Papp, Boston, MA (US); Jan Unkelbach, Boston, MA (US); Thomas Bortfeld, Boston, MA (US); Matthieu Frédéric Bal, Geldrop (NL)

(73) Assignees: KONINKLIJKE PHILIPS N.V., Eindhoven (NL); THE GENERAL HOSPITAL CORPORATION, Boston, MA (US)

( * ) Notice: Subject to any disclaimer, the term of this patent is extended or adjusted under 35 U.S.C. 154(b) by 199 days.

(21) Appl. No.: 15/540,051

(22) PCT Filed: Jan. 20, 2016

(86) PCT No.: PCT/IB2016/050265
§ 371 (c)(1),
(2) Date: Jun. 27, 2017

(87) PCT Pub. No.: WO2016/116868
PCT Pub. Date: Jul. 28, 2016

(65) Prior Publication Data
US 2018/0021594 A1    Jan. 25, 2018

Related U.S. Application Data

(60) Provisional application No. 62/106,250, filed on Jan. 22, 2015.

(51) Int. Cl.
*A61N 5/10*    (2006.01)

(52) U.S. Cl.
CPC ........ *A61N 5/103* (2013.01); *A61N 5/1047* (2013.01); *A61N 5/1081* (2013.01)

(58) Field of Classification Search
CPC ............. A61N 5/103; A61N 5/1081; A61N 2005/1041; A61N 5/1047
See application file for complete search history.

(56) References Cited

U.S. PATENT DOCUMENTS 8,986,186 B2    3/2015    Zhang et al.
2005/0207531 A1    9/2005    Dempsey et al.

FOREIGN PATENT DOCUMENTS

WO    WO-2005072825 A1 *    8/2005    ........... A61N 5/1031
WO    WO-2012024448 A2 *    2/2012    ............ A61N 5/103

OTHER PUBLICATIONS

Becker, S.J. et al., "Collisiion indicator charts for gantry-couch position combinations for Siemens ONCOR and Elekta Infinity Linacs,", Journal of Applied Clinical Medical Physics, 14(5), 2013.
(Continued)

*Primary Examiner* — Christine H Matthews
*Assistant Examiner* — Joshua Daryl D Lannu

(57) ABSTRACT

A method includes determining a set of candidate beam directions. The radiation therapy method further includes selecting a sub-set of non-coplanar beam directions of interest from the set of candidate beam directions based on a fluence optimization using a beam angle selection algorithm. The radiation therapy method further includes determining a set of delivery options based on a beam trajectory algorithm, wherein the delivery options at least include a non-coplanar trajectory during radiation treatment delivery. The radiation therapy method further includes optimizing the delivery options to generate a VMAT radiation plan with
(Continued)

non-coplanar beam trajectories. The optimizing of the delivery options includes optimizing at least one machine parameter.

14 Claims, 2 Drawing Sheets

(56) References Cited

OTHER PUBLICATIONS

Zhu, C. et al., "L-BFGS-B, FORTRAN routines for large scale bound constrained optimization. ACM," Transactions on Mathematical Software, 23(4):550-560, 1997.
Papadimitriou, C.H. et al., "Combinatorial Optimization," Dover, 1998.
Vazirani, V., "Approximation Algorithms," Springer, 2003.
Gurobi, Optimization. Gurobi Optimizer, version 5.6, http://www.gurobi.com/products/gurobi-optimizer/gurobin-overview.
IBM Corp. CPLEX User's Manual, version 12.6.
Papp, D. et al., "Direct leaf trajectory optimization for volumetric modulated arc therapy planning with sliding window delivery," Medical Physics, 41:011701, Jan. 2014.
Smyth, G. et al., "Trajectory optimization for dynamic couch rotation during volumetric modulated arc radiotherapy", Physics in Medicine and Biology, Institute of Physics Publishing, Bristol GB, vol. 58, No. 22, Nov. 7, 2013, pp. 8163-8177.
Meedt, G. et al., "Non-coplanar beam direction optimization for intensity-modulated radiotherapy", Physics in Medicine and Biology, Sep. 21, 2003, pp. 2999-3019.

\* cited by examiner

VOLUMETRIC MODULATED ARC THERAPY (VMAT) WITH NON-COPLANAR TRAJECTORIES

CROSS-REFERENCE TO PRIOR APPLICATIONS

This application is the U.S. National Phase application under 35 U.S.C. § 371 of International Application Serial. No. PCT/IB2016/050265, filed on Jan. 20, 2016, which claims the benefit of U.S. Application Ser. No. 62/106,250, filed on Jan. 22, 2015. These applications are hereby incorporated by reference herein.

FIELD OF THE INVENTION

The following generally relates to radiotherapy delivery, and more particularly Volumetric Modulated Arc Therapy (VMAT) with non-coplanar trajectories.

BACKGROUND OF THE INVENTION

In Intensity Modulated Radiation Therapy (IMRT), the use of non-coplanar beams yields treatment plans with improved organ sparing compared to coplanar plans. Current radiotherapy planning systems have limited support for optimizing non-coplanar incident beam directions in general. This is due in at least part to the combinatorial nature of the problem. Current approaches such as simulated annealing or integer programming are too computationally expensive to be used in practice.

Volumetric Modulated Arc Therapy (VMAT) refers to radiotherapy treatments in which the treatment beam continuously transmits while the gantry (and hence the treatment beam) rotates. VMAT allows for reduced treatment time by delivering radiation while the gantry moves around the patient. Unfortunately, VMAT delivery has been restricted to coplanar beams, for example, realized by a fixed couch angle, such as zero.

SUMMARY OF THE INVENTION

Aspects described herein address the above-referenced problems and/or others.

In one aspect, a method includes determining a set of candidate beam directions. The radiation therapy method further includes selecting a sub-set of non-coplanar beam directions of interest from the set of candidate beam directions based on a fluence optimization using a beam angle selection algorithm. The radiation therapy method further includes determining a set of delivery options based on a beam trajectory algorithm, wherein the delivery options at least include a non-coplanar trajectory during radiation treatment delivery. The radiation therapy method further includes optimizing the delivery options to generate a VMAT treatment plan with non-coplanar beam trajectories. The optimizing of the delivery options includes optimizing at least one machine parameter.

In another aspect, a radiation treatment system includes a candidate beam direction determiner configured to determine a set of candidate beam directions. The system further includes a beam direction selector configured to selects sub-set of non-coplanar beam directions from the set of candidate beam directions based on a fluence optimization using a beam angle selection algorithm. The system further includes a beam trajectory determiner configured to determine a set of delivery options that at least include a delivery that involves both beam rotation and subject support rotation during volumetric arc delivery. The system further includes a plan optimizer configured to optimize the delivery options, which generates a VMAT radiation plan with non-coplanar beam directions.

In another aspect, a non-transitory computer readable medium is encoded with computer executable instructions, which when executed by a processor, causes the processor to: determine a set of candidate beam directions, select a sub-set of non-coplanar beams from the set of candidate beam directions based on a fluence optimization using a beam angle selection algorithm, determine a set of delivery options based on a beam trajectory algorithm, wherein the delivery options at least include: a delivery that involves both beam rotation and a subject support rotations during volumetric arc delivery, optimize the delivery options, which generates a VMAT radiation plan with non-coplanar beam directions, and control a radiation treatment system in VMAT mode to continuously deliver radiation based on non-coplanar trajectories while rotating the beam and rotating the subject support based on the signal.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
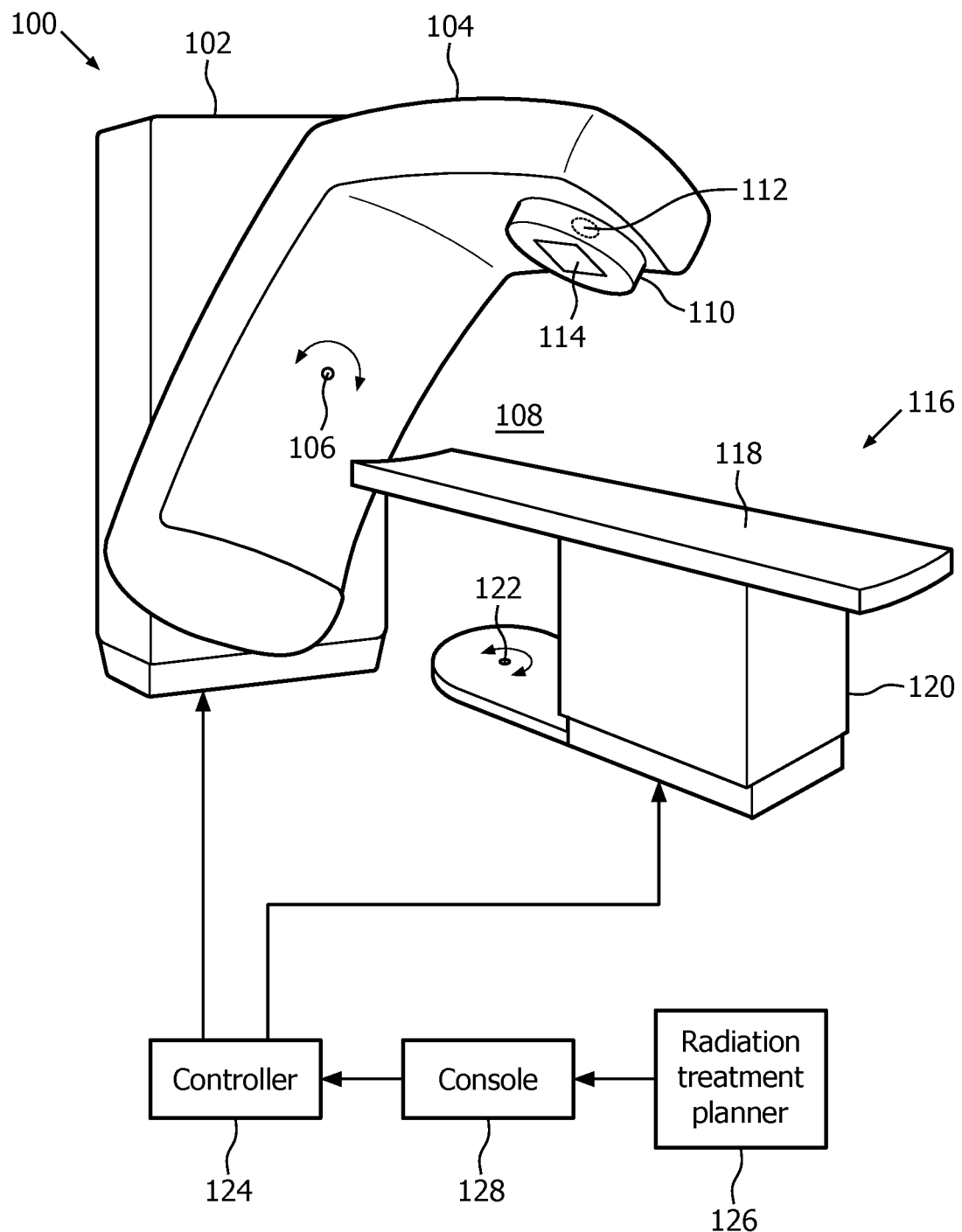
FIG. 1 schematically an example radiation therapy system that includes a radiation treatment planner configured to generate VMAT with non-coplanar trajectories plans.

FIG. 1 schematically illustrates a radiation therapy system 100 such a linear accelerator, or linac. The radiation therapy system 100 includes a stationary gantry 102 and a rotating gantry 104, which is rotatably attached to the stationary gantry 102. The rotating gantry 104 rotates (e.g., 180°, etc.) with respect to a rotation axis 106 about a treatment region 108.

The stationary gantry 102 includes a treatment head 110 with a therapy (e.g., a megavolt (MV) radiation source 112 that delivers treatment radiation and a collimator 114 (e.g., a multi-leaf collimator) that can shape the radiation fields that exit the treatment head 110 into arbitrary shapes. The radiation source 112 rotates in coordination with the rotating gantry 104 about the treatment region 108. The collimator 114 includes a set of jaws that can move independently to shape a field.

A subject support 116, such as a couch, supports a portion of a subject in the treatment region 108. The illustrated patient support 116 includes a tabletop 118 configured to translate in and out of the treatment region 108 and a base 120 configured to rotate about a pivot point 122, which rotates the patient in a plane perpendicular to a plane of rotation of the treatment head 110 and the megavolt radiation source 112.

A controller 124 is configured to control simultaneous rotation of the rotating gantry 104 and the subject support 116 and continuous deliver of treatment radiation by the megavolt radiation source 112 during a treatment (e.g., VMAT mode). The controller 124 is also configured to control the system 100 for one or more other modes such as step and shoot delivery at a set of beam positions, combined volumetric arc and step-and-shoot delivery and one or more co-planar or non-coplanar arc deliveries.

A radiation treatment planner 126 creates radiation treatment plans. This includes a treatment plan with beam trajectories for non-coplanar beams for VMAT mode. As described in greater detail below, the radiation treatment planner 126 employs a computationally efficient iterative approach to determine non-coplanar trajectories for VMAT mode using a combinatorial optimization model. This includes adaptation of coplanar arc therapy planning algorithms to the more complex non-coplanar treatment planning setting. The approach also allows imposing practical delivery limitations of the machine and adjusting the trade-off between treatment time and treatment plan quality. As such, the system 100 allows for reduced treatment time, relative to IMRT mode, while with improved organ sparing compared to coplanar plans.

It is to be appreciated that the radiation treatment planner 126 can be implemented via one or more processors (e.g., micro-processor, central processing unit, controller, etc.) executing one or more computer readable instructions. In one instance, the one or more computer readable instructions are encoded on non-transitory computer readable storage medium such a physical memory and/or other non-transitory medium. Additionally or alternatively, at least one of the computer readable instructions can be carried by a carrier waver, a signal and/or other transitory medium.

An operator console 128 includes human readable output devices such as a display and input devices such as a keyboard and/or mouse. Software accessible on the console 128 allows the operator to control an operation of the radiation therapy system 100. For example, an operator can select and load a treatment plan for VMAT mode with non-coplanar beam (or coplanar beam, IMRT mode with non-coplanar beam or coplanar beam, etc.). In response thereto, the console 128 transmits a command signal to the controller 124, which causes the controller 124 to simultaneously rotate the rotating gantry 104 and the subject support 116, while the radiation source 112 continuously delivers radiation.

Figure 2:
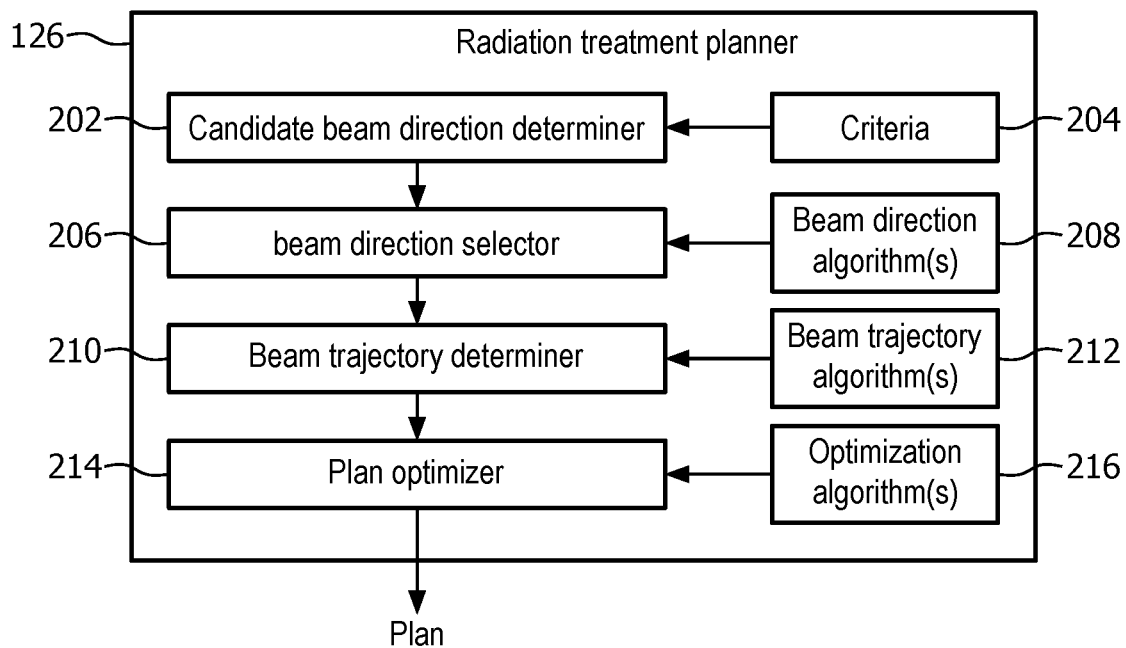
FIG. 2 schematically illustrates an example of the radiation treatment planner.

FIG. 2 illustrates a non-limiting example of the radiation treatment planner 126.

The radiation treatment planner 126 includes a candidate beam direction determiner 202. The candidate beam direction determiner 202 determines a set of candidate beam directions, taking into account predetermined criteria 204. Examples of the predetermined criteria 204 include a collision of the rotating gantry 104 with the subject support 116 and a collision of the rotating gantry 104 with a subject supported by the subject support 116. Other criteria 204 may prohibit certain beams even if they are collision free. For example, some machines may not allow posterior-inferior beams (i.e. rotating the gantry beyond 180° towards the table if the couch is at ±90°.

Other criteria may include requiring the beam not to enter through a missing CT slice and/or the beam to be a "favorable" beam. An example of an "unfavorable" beam is a superior-inferior beam that leads to a large exit dose in the patient, a beam that enters through the eyes, etc. Excluding instead of penalizing unfavorable beams prior to determining the candidate beam direction may reduce the number of candidate beams from the outset and thus reduce computation time. However, exclusion of unfavorable beams can also be achieved during optimization. Other criteria are also contemplated herein.

Excluding beams based on collisions of the rotating gantry 104 with the subject support 116 and certain beams even if they are collision free can be achieved through a machine model. For excluding beams based on collisions of the rotating gantry 104 with the patient, generation of charts with collision free angles depending on table translation and a generic patient model may be utilized. An example of this is discussed in Becker et al., "Collision indicator charts for gantry-couch position combinations for Siemens ONCOR and Elekta Infinity linacs," Journal of Applied Clinical Medical Physics, 14(5), 2013.

The radiation treatment planner 126 further includes a beam direction selector 206. The beam direction selector 206 selects a set of non-coplanar beam directions based the set of candidate beam directions and/or other beam directions such as already selected beam positions, which can be an empty set in a first iteration. For this, the beam direction selector 206 identifies, based on one or more beam direction determining algorithms 208, a sub-set of the candidate beam directions as the set of non-coplanar beam directions.

In one instance, the set of non-coplanar beam directions is identified based on a fluence optimization. An example fluence optimization is shown in EQUATION 1:

$$\text{Minimize } F(d), \qquad \text{EQUATION 1:}$$

where d represents a dose distribution and F is an objective function quantifying deviation of the dose distribution d from treatment goals. The dose distribution d can be determined as shown in EQUATION 2:

$$d = \Sum_{b \in C \subset B} D^b(x^b - x_{ref}^b) + M(x_{ref}), \qquad \text{EQUATION 2:}$$

where B represents the set of candidate beam directions, C represents the identified sub-set of the received set of candidate beam directions, b represents a beam index, $x^b$ represents a vector of beamlet intensities for the beam b, $D^b$ represents a corresponding dose-fluence matrix, M represents a dose computation method, for instance collapsed cone convolution or Monte Carlo based method that is used in combination with a beamlet based more approximate dose computation approach, and $x_{ref}$ represents a set of reference fluence intensities, which are indexed with b.

At least one of the algorithms 208 defines an iterative beam angle selection approach in which beam directions are identified and added to the treatment plan successively. For example, in one instance in iteration n the treatment plan consists of the beam set $C_n$, which includes n beams. In order to select a next beam, each remaining candidate beam $b \subset B/C_n$ is added separately to an ensemble, and the beam direction selector 206 solves EQUATION 1.

Subsequently, a candidate beam that yields a lowest objective function value is added to the beam ensemble $C_n$. This approach is referred to herein as a "greedy" beam angle selection approach as in every iteration it myopically selects the beam that yields the greatest immediate improvement. This approach can yield comparable plan quality compared to stochastic search approaches for beam angle optimization. The following describes example approximations that can speed up the iterative beam selection.

In one approach (referred to herein as a "lookahead" approach), the beam direction selector 206 solves EQUATION 1 only approximately by performing a small number (e.g., 5, 10, 20, 50, etc.) of iterations of a gradient descent based algorithm. The objective function value reached after a fixed number of iterations represents a score for the quality of a candidate beam. In one example, an extension to the Limited-memory Broyden-Fletcher-Goldfarb-Shannon (L-BFGS) optimization is used. The L-BFGS optimization is in a family of quasi-Newton methods that approximates the Broyden-Fletcher-Goldfarb-Shanno (BFGS) algorithm using a limited amount of computer memory.

The extended approach (L-BFGS-B) extends L-BFGS to bound-constrained problems, which requires only first-order information from the optimization objective (that is, the objective function value and its gradient needs to be computed in every iteration, but not the Hessian). As such, this approach can be used within beam angle selection using the lookahead strategy. The L-BFGS-B approach is discussed in Zhu et al., "L-BFGS-B, FORTRAN routines for large scale bound constrained optimization. ACM," Transactions on Mathematical Software, 23(4):550-560, 1997.

In another approach (referred to herein as a "gradient norm" approach), the beam direction selector 206 selects the beam angle by considering only the norm of the gradient of the objective function in the first iteration to obtain a beam score. More particularly, the projection of the negative of the gradient of the objective function indicates the rate at which the objective function decreases as a weight of a newly added beam increases. This is akin to a standard variable selection approach in column generation methods used in convex optimization.

With this approach, the beam angle selection process is further simplified by considering only the gradient of the objective function in the first iteration. After adding the previous beam, the fluence maps of all beams in $C_n$ are fixed at their optimal values, while the new candidate beam b has zero fluence. The projected negative gradient of the objective function $(-\nabla F(d)_+$, which is a steepest feasible descent direction at the current solution. For example, for every candidate beam $b \notin C_n$, the norm of the vector is calculated as shown in EQUATION 3:

$$\|-\nabla F(d)_+\| = \sqrt{\sum_j \left[\max\left(0, -\frac{\partial F}{\partial x_j^b}\right)\right]^2}, \qquad \text{EQUATION 3}$$

which serves as a first-order estimate of the improvement in the optimal value of F that results from adding beam b to the beam ensemble $C_n$. The partial derivatives with respect to the beamlet intensities are zero for all beamlets included in $C_n$ for which the non-negativity constraint is not binding. The candidate beam with a largest value of the projected gradient norm is added to the beam ensemble.

In both the "lookahead" approach and the "gradient norm" approach, the beam direction selector 206 adds the beam with the best score. Subsequently, the beam direction selector 206 solves EQUATION 1 for the new beam ensemble, and the fluence maps of all beams are fixed to their optimal value before the next beam is selected. Once the set of non-coplanar beam directions are selected, the resulting beam angles serve as anchor points of the arc therapy trajectory described next.

An additional approach to select a new beam includes solving with the selected beam positions and all candidate beam positions. For this, the objective values obtained are compared with the full set minus one of the candidate beam positions. The removal that causes the largest degradation of the objective value identifies a candidate beam position of interest to the currently found solution.

The radiation treatment planner 126 further includes a beam trajectory determiner 210, which determines a set of delivery options based on a beam trajectory algorithm(s) 212. The delivery options can include: 1) step and shoot delivery at the set of beam positions; 2) combined volumetric arc and step-and-shoot delivery; 3) one or more co-planar or non-coplanar arc deliveries, and/or 4) a delivery that involves both gantry and the subject support 116 rotations during volumetric arc delivery. The difference between candidate delivery trajectories can include the number and/or amount of the subject support 116 movements.

For delivery that involves both rotating gantry 104 and subject support 116 rotations during volumetric arc delivery, finding a shortest beam trajectory that passes through prescribed beam angles is a variant of a combinatorial optimization problem. That is, for each pair of beam angles, a distance can be defined as a least amount of time needed to reposition the rotating gantry 104 and the subject support 116 from one angle to the other. The beam trajectory of interest is a shortest path that visits each beam angle, without necessarily returning to the first beam angle.

This trajectory can be determined by the order (or permutation) in which the beam angles are visited. In one instance, a highest safe gantry and subject support rotation speed are approximately the same, and the rotating gantry 104 and the subject support 116 rotate simultaneously. With this instance, a length of every trajectory can be measured in degrees instead of time, and a metric for a distance between two (couch, gantry) positions $(c_1, g_1)$ and $(c_2, g_2)$ can be found using EQUATION 4:

$$\max(|c1-g1|, |c2-g2|). \qquad \text{EQUATION 4:}$$

For instance, a trajectory that has length 360 degrees is traceable in the same amount of time as a full coplanar gantry arc with no subject support rotation. The distance metric could be modified if necessary. For example, by assuming a slower couch speed, trajectories with less subject support 116 rotation are favored at the price of more rotating gantry 104 motion. Similarly, a shortest trajectory connecting two wildly different collision-avoiding pairs could lead to collision. Trajectory lengths could use a length of a shortest collision-avoiding path connecting $(c_1, g_1)$ and $(c_2, g_2)$ in place of EQUATION 4, which can be computed using established shortest path algorithms.

To find a beam trajectory of approximately prescribed length, the "lookahead" approach is used to identify beam angles one by one. After the addition of a beam angle to the ensemble, the shortest trajectory visiting each of these angles is determined. Non-limiting examples of approaches that can be used to determine the shortest trajectory visiting each of these angles are discussed in Papadimitriou et al., "Combinatorial Optimization," Dover, 1998, and Vazirani, "Approximation Algorithms," Springer, 2003. Example stopping criterion can be used to continue while this trajectory is shorter than a coplanar 360-degree arc. This allows for finding non-coplanar VMAT plans deliverable in approximately the same amount of time as a full coplanar VMAT arc.

Although this approach and its variants are Non-deterministic Polynomial-time (NP)-hard, they can be solved for a small number of beam angles, such as 10-20 beam angles. These instances can be solved readily quickly (e.g., within a fraction of the second) using known integer programming solvers, such as CPLEX or GUROBI and/or other solvers. Examples of such solvers are discussed in Gurobi, "Optimization. Gurobi Optimizer, version 5.6," http://www.gurobi.com/products/gurobi-optimizer/gurobi-overview, and IBM Corp. CPLEX User's Manual, version 12.6. http://pic.dhe.ibm.com/infocenter/cosinfoc/v12r6/topic/ilog.odms.cplex.help/CPLEX/homepages/usrmancplex.html.

The beam trajectory determiner 210 determines a final beam trajectory using the anchor points and the optimized sequence in which they are visited, e.g., for the case where both the subject support 116 and the rotating gantry 104 move at constant speed between anchor points. For the final planning, the beam trajectory determiner 210 uses dose-influence matrices along the beam trajectory for a predetermined resolution. To that end, the full trajectory, in one non-limiting instance, is divided into a number of segments (e.g., 180, more, or less) that are spaced (e.g., equally or not equally) regarding a modulation by the leaves and the angular sensitivity of the dose computation.

The radiation treatment planner 126 further includes a plan optimizer 214 that optimizes the plan based on an optimization algorithm(s) 216. In one instance, the optimizing includes optimizing further machine parameters such as MLC leaf positions and/or other machine parameters. Once the beam trajectory is fixed, the final plan can be obtained by adapting a VMAT algorithm previously developed for coplanar VMAT. A VMAT optimization does not inherently rely on coplanar beam trajectories and can be generalized to a given non-coplanar trajectory. One approach is to use a sliding window VMAT optimization algorithm 216.

In this approach, the arc is divided into K arc sectors. In each arc sector, the MLC leaves move unidirectionally across the field, delivering an intensity-modulated field. Given sufficient treatment time, the plan quality of a coplanar VMAT plan with K leaf sweeps approaches the plan quality of a K-beam IMRT plan with equi-spaced beams. An example of such an approach is discussed in Papp et al., "Direct leaf trajectory optimization for volumetric modulated arc therapy planning with sliding window delivery," Medical Physics, 41:011701, Jan. 2014.

Variations are contemplated.

In a variation, the acceleration of the subject support 116 is incorporated into the delivery time. A large (de)acceleration is to be avoided as it is uncomfortable for the patient and increases the uncertainty in the patient position during delivery.

In another variation, the trajectory of the deliveries could be based on a library of allowed trajectories, on a collection of already approved plans created for other patients or on those trajectories that only involve very limited couch movements and or accelerations.

In still another variation, the potential trajectories determined do not need to exactly overlap with the selected beam positions.

Figure 3:
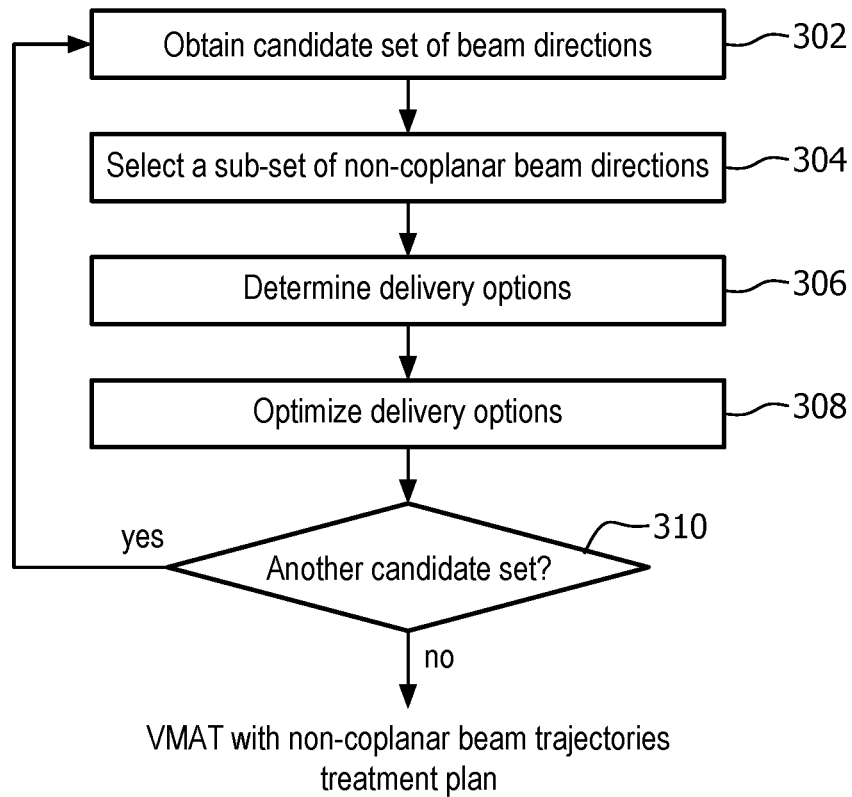
FIG. 3 illustrates an example method for VMAT) with non-coplanar trajectories.

FIG. 3 illustrates an example method for VMAT) with non-coplanar trajectories.

It is to be appreciated that the ordering of the acts in the methods described herein is not limiting. As such, other orderings are contemplated herein. In addition, one or more acts may be omitted and/or one or more additional acts may be included.

At 302, a candidate set of beam directions of interest is obtained, as described herein and/or otherwise.

At 304, a sub-set of non-coplamar beam directions of interest are obtained from the candidate set of beam positions of interest, as described herein and/or otherwise.

At 306, delivery options are determined based on the sub-set of beam directions of interest, as described herein and/or otherwise.

At 308, the delivery options are optimized, as described herein and/or otherwise.

At 310, it is determined if there is another candidate set of beam directions of interest to process. If so, acts 302-310 are repeated with the selected set and the new candidate set. If not, a VMAT radiation treatment plan with non-coplanar trajectories is created and conveyed to the console 128 to control the radiation treatment system 100.

The method herein may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

In one non-limiting instance, the radiation therapy system 100 has only one rotation axis/degree of freedom of the beam positions during VMAT delivery. In another non-limiting instance, the radiation therapy system 100 has more than one degree of freedom, which can be used in combination or without a rotation of the subject support 116.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method comprising:
   determining a set of candidate beam directions;
   selecting a sub-set of non-coplanar beam directions of interest from the set of candidate beam directions based on a fluence optimization using a beam angle selection algorithm;
   determining a set of delivery options based on a beam trajectory algorithm, wherein the delivery options at least include a non-coplanar trajectory during radiation treatment delivery; and
   optimizing the delivery options to generate a radiation plan with non-coplanar beam trajectories, wherein the optimizing of the delivery options includes optimizing at least one machine parameter,
   wherein the fluence optimization is based on: minimize F(d), where d is a variable that is a representation of a value of a dose distribution and F is an objective function quantifying deviation of the dose distribution d from treatment goals, wherein the dose distribution d is determined by:

$$\Sigma_{b \in C \subset B} D^b(x^b - x_{ref}^b) + M(x_{ref}),$$

where B is a variable that is a representation of a set of candidate beam directions, C is a variable that is a representation of sub-set of candidate beam directions B, b is a variable that is a representation of a value of a beam index, $x^b$ is a variable that is a representation of a vector of beamlet intensities for a beam index b, $D^b$ is a variable that is a representation of a corresponding dose-fluence matrix, M is a dose computation method, and $x_{ref}$ is a variable which is a representation of a set of reference fluence intensities, which are indexed with beam index b,
   wherein the treatment radiation plan consists of a beam set $C_n$, which includes n beams, where n is a positive an integer, and further comprising:
   adding, separately, each remaining candidate beam b ⊂ B/$C_n$ to the beam set $C_n$;
   solving minimize F(d);

identifying a candidate beam that yields a lowest objective function value; and
adding the candidate beam that yields the lowest objective function value to the beam set $C_n$,
wherein minimize F(d) is only approximated by performing a predetermined first number of iterations of a gradient descent algorithm, wherein the objective function value reached after the predetermined first number of iterations represents a score for a quality of a candidate beam,
wherein the method further comprises:
selecting a beam angle based on only a norm of a gradient of the objective function in an iteration to obtain a beam score;
adding the candidate beam to the beam set $C_n$; and
fixing fluence maps of all beams of the beam set $C_n$ at their optimal values while a new candidate beam b has zero fluence.

2. The method of claim 1, wherein the at least one machine parameter includes multi-leaf collimator leaf positions.

3. The method of claim 1, further comprising:
transmitting the radiation plan to a controller that controls a radiation treatment system to continuously deliver radiation based on non-coplanar trajectories while rotating the beam based on the radiation plan.

4. The method of claim 1, further comprising delivering radiation via a radiation treatment system to a subject, wherein the set of candidate beam directions is determined taking into account predetermined criteria, wherein the predetermined criteria includes at least one or more of avoiding a collision of a rotating gantry of a treatment system with a subject support of the radiation treatment system or avoiding a collision of a rotating gantry of the radiation treatment system with the subject supported by the subject support.

5. The method of claim 1, further comprising: iteratively selecting beam angles by identifying and adding an additional candidate beam to the radiation plan successively.

6. The method of claim 1, further comprising:
calculating a norm by:

$$\|-\nabla F(d)_+\| = \sqrt{\sum_j \left[\max\left(0, -\frac{\partial F}{\partial x_j^b}\right)\right]^2},$$

where $-\nabla F(d)_+$ is a projected negative gradient of the objective function, which is a steepest feasible descent direction at a current solution; and
adding a candidate beam with a largest value of a projected gradient norm to the beam set $C_n$.

7. The method of claim 6, further comprising:
finding a fastest beam trajectory that passes through prescribed beam positions by defining a least amount of time needed to reposition a rotating gantry of a radiation therapy system and a subject support of the radiation therapy system from a first position to a second position, wherein a beam trajectory of interest is a fastest path that visits each beam position.

8. The method of claim 7, further comprising:
determining a delivery time of every trajectory in seconds;
determining a travel time between two positions $(c_1, g_1)$ and $(c_2, g_2)$;
finding a beam trajectory of a predetermined maximum time by identifying beam positions one by one;
adding a candidate beam to the beam set;
determining a shortest trajectory visiting each of the beam positions;
finding a final beam trajectory using anchor points and a sequence in which they are visited; and
determining the radiation plan using dose-influence matrices along a beam trajectory for a predetermined resolution.

9. The method of claim 8, further comprising:
finalizing the plan optimizer by adapting a Volumetric Modulated Arc Therapy (VMAT) algorithm previously developed for coplanar VMAT.

10. The method of claim 9, further comprising:
optimizing the radiation plan using a sliding window VMAT optimization algorithm by dividing an arc into K arc sectors, and in each of the K arc sectors, and,
delivering an intensity-modulated field by moving leaves of a collimator unidirectionally across a field.

11. A radiation treatment system, comprising:
a candidate beam direction determiner configured to determine a set of candidate beam directions;
a beam direction selector configured to select a sub-set of non-coplanar beam directions from the set of candidate beam directions based on a fluence optimization using a beam angle selection algorithm;
a beam trajectory determiner configured to determine a set of delivery options that at least include a delivery that involves both beam rotation and subject support rotation during volumetric arc delivery; and
a plan optimizer configured to optimize the delivery options, which generates a Volumetric Modulated Arc Therapy (VMAT) radiation plan with non-coplanar beam directions,
wherein the fluence optimization is based on: minimize F(d), where d is a variable that is a representation of a dose distribution and F is an objective function quantifying deviation of the dose distribution d from treatment goals, wherein the dose distribution d is determined by:

$$d = \Sigma_{b \in c \subset B} D^b x^b,$$

where B is a variable that is a representation of a set of candidate beam directions, C is a variable that is a representation of a sub-set of candidate beam directions B, b is a variable that is a representation of a value of represents a beam index, $x^b$ is a variable that is a representation of a vector of beamlet intensities for a beam b, and $D^b$ is a variable that is a representation of a corresponding dose-fluence matrix,
wherein the beam direction selector approximates minimize F(d) by performing a predetermined first number of iterations of a gradient descent algorithm, wherein an objective function value reached after the predetermined first number of iterations represents a score for a quality of a candidate beam, or
wherein the beam direction selector selects the beam angle based on a norm of a gradient of the objective function in an iteration to obtain a beam score, add the beam to a beam set $C_n$, fix the fluence maps of all beams of the beam set $C_n$ at their optimal values while a new candidate beam b has zero fluence.

12. The radiation treatment system of claim 11, wherein the beam trajectory determiner finds a shortest beam trajectory that passes through prescribed beam angles by defining a distance as a least amount of time needed to reposition a rotating gantry of a radiation therapy system and a subject support of the radiation therapy system from a first beam angle to a second beam angle, wherein a beam trajectory of interest is a shortest path that visits each beam angle, without returning to the first beam angle.

13. The radiation treatment system of claim 11, wherein the plan optimizer optimizes the plan using a sliding window VMAT optimization algorithm by dividing an arc into K arc sectors, and in each of the K arc sectors, and further including a collimator having leaves which move unidirectionally across a field, delivering an intensity-modulated field.

14. A non-transitory computer readable medium encoded with computer executable instructions, which when executed by a processor, causes the processor to:
determine a set of candidate beam directions;
select a sub-set of non-coplanar beams from the set of candidate beam directions based on a fluence optimization using a beam angle selection algorithm;
determine a set of delivery options based on a beam trajectory algorithm, wherein the delivery options at least include: a delivery that involves both beam rotation and a subject support rotations during volumetric arc delivery;
optimize the delivery options, which generates a VMAT radiation plan with non-coplanar beam directions; and
control a radiation treatment system in VMAT mode to continuously deliver radiation based on non-coplanar trajectories while rotating at least one candidate beam and rotating the subject support based on the radiation plan,
wherein the fluence optimization is based on: minimize F(d), where d is variable that is a representation of a dose distribution and F is an objective function quantifying deviation of the dose distribution d from treatment goals, wherein the dose distribution d is determined by:

$$d = \Sigma_{b \in c \subset B} D^b x^b,$$

where B is a variable which is a representation of a set of candidate beam directions, C is a variable which is a representation of a sub-set of candidate beam directions B, b is a variable which is a representation of a beam index, $x^b$ is a variable of a representation of a vector of beamlet intensities for the beam b, and $D^b$ is a variable that is a representation of a corresponding dose-fluence matrix,
wherein minimize F(d) is approximated by performing a predetermined first number of iterations of a gradient descent algorithm, wherein the objective function value reached after the predetermined first number of iterations represents a score for a quality of a candidate beam, or
wherein the beam angle is selected based on a norm of a gradient of the objective function in an iteration to obtain a beam score, the beam is added to a beam set $C_n$, the fluence maps of all beams of the beam set $C_n$ are fixed at their optimal values while a new candidate beam b has zero fluence.

* * * * *